US006780979B1

(12) United States Patent
Deslys

(10) Patent No.: US 6,780,979 B1
(45) Date of Patent: Aug. 24, 2004

(54) METHOD FOR PURIFYING PRPRES FROM A BIOLOGICAL SAMPLE AND APPLICATIONS

(75) Inventor: Jean-Philippe Deslys, Le Chesnay (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/622,421

(22) PCT Filed: Feb. 16, 1999

(86) PCT No.: PCT/FR99/00338

§ 371 (c)(1),
(2), (4) Date: Oct. 13, 2000

(87) PCT Pub. No.: WO99/41280

PCT Pub. Date: Aug. 19, 1999

(30) Foreign Application Priority Data

Feb. 16, 1998 (FR) .............................. 98 01823

(51) Int. Cl.[7] .............................. G07K 1/14; G07K 1/22; G01N 33/53
(52) U.S. Cl. ....................... 530/412; 530/413; 530/427; 435/7.1; 435/962; 435/975
(58) Field of Search ................................. 530/412, 418, 530/422, 427, 413; 435/7.1, 975, 962

(56) References Cited

U.S. PATENT DOCUMENTS 4,289,690 A * 9/1981 Pestka et al. ............... 530/351
4,894,436 A * 1/1990 Auerswald et al. ......... 530/324
6,150,172 A * 11/2000 Schmerr et al. ............ 530/350

FOREIGN PATENT DOCUMENTS

WO    WO 98/30909    7/1998

OTHER PUBLICATIONS

Parekh et al., Analytical Biochem., 1985, 148(1):87–92.*
Caughey et al., J. of Virol., 1991 65(12):6597–603.*

Caughey, B. et al., "N–Terminal truncation of the scrapie–associated form of PrP by Iysosomal protease (x): implications regarding the conversion of PrP to the protease–resistant state", *Journal of Virology*, vol. 65, No. 12, Dec. 1991, pp. 6597–6603 (abstract only).

Chen, S.G. et al., "Allelic origin of the abnormal prion protein isoform in familial prion diseases", *Nature Medicine*, vol. 3, No. 9, Sep. 1997, pp. 1009–1015.

Lehman, S. et al., "Two mutant prion proteins expressed in cultured cells acquire biochemical properties reminiscent of the scrapie isoform", *Proceedings of the National Academy of Sciences of U.S.A.*, vol. 93, May 1996, pp. 5610–5614.

McKinley, M.P. et al., "Scrapie prion rod formation in vitro requires both detergent extraction and limited proteolysis", *Journal of Virology*, vol. 65, No. 3, Mar. 1991, pp. 1340–1351 (abstract only).

* cited by examiner

*Primary Examiner*—Lorraine Spector
*Assistant Examiner*—Jegatheesan Seharaseyon
(74) *Attorney, Agent, or Firm*—Morgan, Lewis & Bockius LLP

(57) ABSTRACT

The invention concerns a method for purifying PrPres from a biological sample to be used for qualitative and/or quantitative determination of the PrPres in said sample. The method essentially consists in: (1) incubating, during 30 seconds to 2 hours, at a temperature less than 80° C., said biological sample with a buffer solution A comprising at least a surfactant in an amount ranging between a quarter and four times the weight of the biological sample and optionally a protease, to form a suspension S1; (2) adding to said suspension S1 resulting from (1) a buffer solution B in an amount sufficient for thinning said suspension, which buffer solution B consists of a solvent or mixture of solvents, which does not solubilize the PrPres and has a constant dielectric ranging between 10 and 25; (3) centrifuging the suspension S2 resulting from step (2); and (4) solubilizing said pellet in a buffer solution C comprising at least a surfactant and/or at least a chaotropic agent, at a temperature ranging between room temperature and 100° C.

20 Claims, 6 Drawing Sheets

METHOD FOR PURIFYING PRPRES FROM A BIOLOGICAL SAMPLE AND APPLICATIONS

Figure 1:
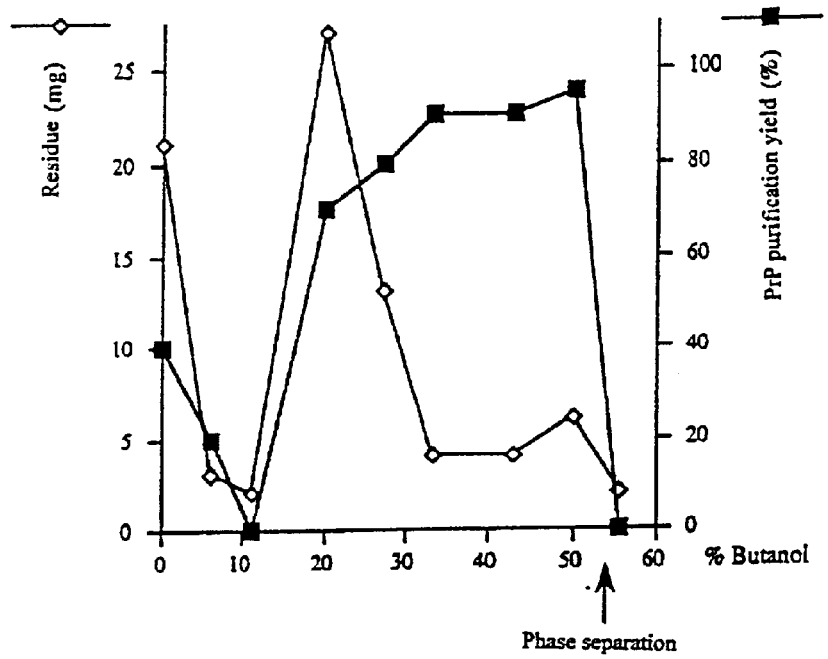

The present invention relates to a novel method of purifying PrPres from a biological sample in order to use it for the qualitative and/or quantitative detection of PrPres in said sample.

Transmissible subacute spongiform encephalopathies are caused by non-conventional transmissible agents (NCTA), also called prions, the precise nature of which is still unknown at the present time. TSSE comprise essentially Creutzfeldt-Jakob disease (CID) in humans, scrapie in sheep and goats and bovine spongiform encephalopathy (BSE) in cattle; other encephalopathies have been revealed in mink or certain wild animals such as stag and elk.

The outcome of these diseases is inevitably fatal and no effective treatment is currently available.

In transmissible subacute spongiform encephalopathies, there is an accumulation of a host protein, PrP (or prion protein), in an abnormal form (PrPres), mainly in the central nervous system; PrPres copurifies with the infectiousness and its accumulation precedes the appearance of histological lesions. In vitro it is toxic to neuron cultures.

Two biochemical properties usually make it possible to distinguish between PrPres and normal PrP: PrPres is partially resistant to proteases and is insoluble in anionic surfactants.

To be able to detect the PrPres present in a sample, it is necessary to subject said sample to different operations in order to enrich it in PrPres, while eliminating the normal PrP, so that the PrPres can then be detected by any appropriate specific method without causing:

false positives due to the presence of normal PrP or other contaminants, or false negatives due to an insufficient concentration of PrPres in the final biological sample.

A number of methods of isolating and/or purifying PrPres have been proposed for this purpose. They are essentially based on the method developed by Hilmert and Diringer (Nature, 1983, 306, 476–478) and generally involve an extraction with a detergent, differential ultracentriugations and a treatment with proteolytic enzymes (Multhaup G. et al., EMBO J., 1985, 4, 6, 1495–1501; Takahashi K et al., Microbiol. Immunol., 1986, 30, 2, 123–131; Hope J. et al., EMBO J., 1986, 5, 10, 2591–2597; Grathwohl K. U. D. et al., Arch. Virol., 1996, 141, 1863–1874; Kascsak R. J. et al., Immunol. Investig., 1997, 26, 259–268; R. E. Race et al., J. Gen. Virol., 1992, 73, 3319–3323; Doi et al., J. Gen. Virol., 1988, 69, 955–960; T. Muramoto et al., Am. J. Pathol., 1993, 143, 5, 1470–1479; Farquhar C. F. et al., Gen. Virol., 1994, 75, 495–504 and J. Gen. Virol., 1996, 77, 1941–1946). They have the disadvantage of comprising a large number of steps including several ultracentrifugations, which are cumbersome to carry out and result in cumulative losses of PrPres; these in turn lead to an insufficient sensitivity to obtain a high-quality detection threshold and quantification of the PrPres.

These various methods require research laboratory equipment and implementation times which are incompatible with use in the field, particularly in abattoirs.

Now, there is a need for rapid verification of the absence or presence of a transmissible subacute spongiform encephalopathy at the time when the animal is slaughtered.

Consequently the inventor set out to provide a method of purifying a biological sample in order to use it for a rapid and reliable detection of PrPres, said method being sufficiently simple to carry out that it can be used in the field, especially in abattoirs, and thereby meeting practical needs better than the methods of the prior art. In fact, the method according to the invention is:

simple to carry out, reliable and easy to interpret it increases the detection sensitivity threshold of PrPres by eliminating the false positives (normal PrP and other contaminants), and it eliminates the false negatives because it enables a substantial amount of PrPres to be obtained, in absolute terms, since it is possible to treat large amounts of biological material with a purification yield in excess of 80%; this is of particular value in abattoirs and produces samples in which PrPres is readily detectable with customary diagnostic tests.

The present invention relates to a method of purifying PrPres from a biological sample, characterized in that it comprises essentially:

(1) the incubation, for 30 seconds to 2 hours, preferably for 30 seconds to 10 minutes, at a temperature below 80° C., of said biological sample with a buffer A comprising at least one surfactant in an amount of between a quarter and four times, preferably of between a quarter and one and a half times, the weight of the biological sample, and optionally prior, subsequent or simultaneous incubation with a protease, to form an opalescent to turbid micellar or lamellar suspension S1; under the temperature and quantity conditions mentioned above, whatever the surfactant or surfactant mixture may be, it does not solubilize most of the PrPres, which remains in suspension, whereas the normal PrP is solubilized, or even destroyed, if protease is added; said incubation is preferably carried out at a temperature below 50° C., in the presence of an amount of surfactant of between a quarter and one and a half times the weight of the biological sample; according to the invention, the protease can in fact be added either before, after or simultaneously with the surfactant;

(2) the addition, to said micellar or lamellar suspension S1 obtained in (1), of a buffer B in an amount suitable for clarifying said suspension (for example by forming a microemulsion or a microsuspension), said buffer B consisting of a solvent or solvent mixture which does not solubilize the PrPres and has a dielectric constant of between 10 and 25; this gives a suspension S2 which is limpid to the naked eye;

(3) the centrifugation of the suspension S2 obtained in step (2); said centrifugation is carried out for example for 2 to 10 minutes at a speed below 20,000 g, preferably at a speed of between 3500 g and 17,500 g; the PrPres ends up in the centrifugation residue with a PrPres purification yield surprisingly of between 80 and 100%; advantageously the centrifugation time and speed can be adapted to give the same result, namely a PrPres purification yield of between 80 and 100%; and (4) the solubilization of said residue in a buffer C comprising at least one surfactant, as defined in step (1), at a concentration of between 0.1% and 5%, preferably of between 0.25% and 1%, based on the volume of buffer C (w/v), and/or at least one chaotropic agent at a concentration of between 0.1 M and 8 M, at a temperature between room temperature and 100° C., preferably equal to or greater than 80° C.; under such temperature conditions, the above-mentioned surfactants, preferably ionic surfactants, and/or the chaotropic agents solubilize the PrPres.

Said steps (1) and (2) can be carried out simultaneously or successively; they are preferably carried out successively.

In one advantageous mode of carrying out said method, if the biological sample is a tissue or an organ, it is homogenized prior to step (1), for example by mechanical grinding in a homogenization buffer consisting of a neutral buffer such as water, or an isotonic buffer such as 5% glucose.

In another advantageous mode of carrying out said method, the temperature used in step (1) is between room temperature and 50° C.; it is preferably 37° C.

Buffer A preferably comprises a surfactant selected from the group consisting of:

- anionic surfactants such as SDS (sodium dodecylsulfate), sarkosyl (lauroylsarcosine), sodium cholate, sodium deoxycholate or sodium taurocholate;
- zwitterionic surfactants such as SB 3-10 (decyl sulfobetaine), SB 3-12 (dodecyl sulfobetaine), SB 3-14, SB 3-16 (hexadecyl sulfobetaine), CHAPS or deoxy-CHAPS;
- non-ionic surfactants such as C12E8 (dodecyl octaethylene glycol), Triton X100, Triton X114, Tween 20, Tween 80, MEGA 9 (nonanoylmethylglucamine), octylglucoside, LDAO (dodecyldirethylamine oxide) or NP40; or
- surfactant mixtures such as a mixture of an ionic surfactant and a non-ionic surfactant, especially the mixture SDS/Tween 80 or the mixture sarkosyl/Triton X100, a mixture of two ionic surfactants, such as the mixture SDS/deoxycholate, or a mixture of an ionic surfactant and a witterionic surfactant.

In another advantageous mode of carrying out said method, buffer B is preferably selected from $C_3$–$C_6$ alcohols and alcohol mixtures with a mean theoretical dielectric constant of between 10 and 25. The following alcohols or alcohol mixtures are particularly preferred: butan-1-ol, butan-2-ol, 2-methylpropan-1-ol, isopropanol, isopropanol+pentanol, ethanol+hexanol, butanol+pentanol, etc.

In terms of the present invention, dielectric constant is understood as meaning the static dielectric constant $\epsilon$, measured in static or relatively low frequency fields; it corresponds to the ratio of the electric displacement D to the electric field strength E when an electric field is applied to the solution at a temperature of between 293.15 and 298.15 K.

The dielectric constant of liquids, as defined above, is described more particularly in CRC Handbook of Chemistry and Physics (ed. David R. Lide, 75 th edition, 1994, CRC Press).

For a solvent mixture, mean theoretical dielectric constant is understood as the mean of the dielectric constants of each solvent, weighted by its proportion in the mixture.

Surprisingly the addition of buffer B in step (2) makes it possible to obtain purification yields in excess of 90% under low speed centrifugation conditions; it affords a significant reduction in the amount of final residue, while at the same time maintaining a high yield; advantageously the amount of final residue is preferably less than 10% of the initial weight of biological sample so as to be able to utilize it effectively in an immunoassay, whereas if only buffer A is added, the resulting conditions are those of the prior art, which necessitate an ultracentrifugation in order to obtain sufficient yields of PrPres for the purposes of detection.

It may be noted that purification yields in excess of 80% can also be obtained by varying the centrifugation time and speed: 2 to 10 minutes at a speed below 20,000 g or a period of time reduced in proportion to the increase in the number of g.

Preferably the ratio of the yield of PrPres in the solid phase to the amount of residue recovered after centrifigation of the suspension S2 is greater than 10 when the initial sample corresponds to 100 mg of brain.

As a further preference, buffer C used in step (4) comprises a chaotropic agent which is selected especially from the group consisting of urea and guanidine or a mixture thereof; it is also possible to use any other chaotropic agent.

The urea is preferably at a concentration of between 0.25 and 8 M and the guanidine is preferably at a concentration of between 0.1 and 6 M.

If buffer C is a mixture of at least one surfactant and at least one chaotropic agent, it is preferably selected from the group consisting of the following mixtures: a mixture of SDS and urea, a mixture of sarkosyl and urea, a mixture of deoxycholate and urea, a mixture of sarkosyl and guanidine or a mixture of sarkosyl, guanidine and urea Preferably, in the mixture of SDS and urea, the SDS is at a concentration of 0.25–1% and the urea is at a concentration of 0.25–6 M; in the mixture of sarkosyl and urea, the sarkosyl is at a concentration of between 0.25 and 1% and the urea is at a concentration of between 0.25 and 8 M; in the mixture of sarkosyl and guanidine, the sarkosyl is at a concentration of between 0.25 and 1% and the guanidine is at a concentration of between 0.5 M and 3 M, and in the mixture of sarkosyl, guanidine and urea, the sarkosyl is at a concentration of between 0.25 and 1%, the guanidine is at a concentration of between 0.5 M and 3 M and the urea is at a concentration of between 2 and 6 M.

Laemmli's buffer (4% SDS, 0.1 M Tris-HCl pH 8, 5% sucrose and 2% β-mercaptoethanol) can also be used, especially for western blotting.

The present invention further relates to a method of detecting PrPres in a biological sample, characterized in that it comprises:

- treating said sample as defined above,
- diluting the sample obtained, if necessary, and
- detecting the PrPres by any appropriate analytical method, such as an immunological method (ELISA, western blotting), which produces a specific signal.

The above-mentioned dilution step makes it possible to neutralize buffer C to enable detection of the PrPres by an ELISA method; it is effected for example with a buffer comprising albumin to give a final albumin concentration of between 2 and 10% (w/v), or with a buffer based on 1% deoxycholate, for example.

A biological sample treated in this way contains an effective concentration of PrPres, so the latter can be detected directly in said sample by any analytical method, especially an immunological method.

As a variant, the present invention relates to a method of purifying PrPres from a biological sample, characterized in that it comprises essentially:

(1) the incubation, for 30 seconds to 2 hours, preferably for 30 seconds to 10 minutes, at a temperature below 80° C., of said biological sample with a buffer A comprising at least one surfactant in an amount of between a quarter and four times, preferably of between a quarter and one and a half times, the weight of the biological sample, and optionally prior, subsequent or simultaneous incubation with a protease, to form an opalescent to turbid micellar or lamellar suspension S1; according to the invention, the protease is in fact added either before, after or simultaneously with the surfactant;

(2) the addition, to said micellar or lamellar suspension S1 obtained in (1), of a buffer B in an amount suitable for creating a phase separation, said buffer B consisting of a solvent or solvent mixture which does not solubilize the PrPres and has a dielectric constant of between 10 and 25;

(3) the centrifigation of the suspension obtained in step (2); said centrifugation is carried out for example for 2 to 10 minutes at a speed below 20,000 g, preferably at a speed of between 3500 g and 17,500 g; the PrPres ends up at the interface;

(4) the recovery of the film present at the interface;

(5) the resolubilization of said film with a buffer A without the addition of protease;

(6) the centrifugation of the suspension obtained in step (5) for 2 to 10 minutes at a speed below 20,000 g, preferably at a speed of between 3500 g and 17,500 g; the PrPres ends up in the centrifugation residue with a PrPres purification yield surprisingly of between 70 and 100%; advantageously the centrifugation time and speed can be adapted to give the same result, namely a PrPres purification yield of between 70 and 100%; and (7) the solubilization of said residue in a buffer C comprising at least one surfactant, as defined in step (1), at a concentration of between 0.1% and 5%, preferably of between 0.25% and 1%, based on the volume of buffer C (w/v), and/or at least one chaotropic agent at a concentration of between 0.1 M and 8 M, at a temperature between room temperature and 100° C., preferably equal to or greater than 80° C.; under such temperature conditions, the above-mentioned surfactants, preferably ionic surfactants, and/or the chaotropic agents solubilize the PrPres.

The amounts of buffer B to be added to give a microemulsion, a micro-suspension or phase separation are established with the aid of a range of buffers B, as illustrated for butan-1-ol in FIG. 1; they can vary as a function of buffer A and the constituents selected for buffer B.

As a variant, the solubilization step (step (4) of the first method or step (7) of the second method) in said buffer C comprises heating at a temperature equal to or greater than 80° C. for 5 to 10 minutes, followed by centrifugation, preferably for 2 to 10 minutes, at a speed below 20,000 g, preferably at a speed of between 3500 g and 17,500 g; in this case the PrPres is resolubilized and ends up in the supernatant; under such conditions, the sample obtained is particularly suitable for assaying the PrPres by an ELISA method.

The present invention further relates to a kit for treating a biological sample, characterized in that it comprises, in addition to a buffer for homogenizing said biological sample, appropriate amounts of buffer A, buffer B and buffer C, as defined above.

The present invention further relates to a PrPres detection kit, characterized in that it comprises appropriate amounts of a buffer for homogenizing the biological sample in which the PrPres is to be detected, appropriate amounts of buffer A, buffer B and buffer C, as defined above, and at least one appropriate anti-PrPres antibody.

Apart from the foregoing provisions, the invention also includes other provisions which will become apparent from the following description referring to Examples of how to carry out the method forming the subject of the present invention, and to the attached drawings, in which:

FIG. 1 illustrates the influence of the amount of buffer B (butanol) on the PrPres purification yield (in %) and the amount of residue obtained after centrifugation;

FIG. 2 illustrates the influence of different buffers B on the PrPres purification yield (in %) and the amount of residue obtained after centrifugation;

FIG. 3 illustrates the role of the mean theoretical dielectric constant as defined above, in comparing different alcohol mixtures used as buffet B;

FIG. 4 illustrates an example of the detection of PrPres by western blotting;

FIG. 5 illustrates the sensitivity and yield of the ELISA on different dilutions of treated samples according to the invention;

FIG. 6 illustrates an ELISA performed directly on homogenates; and

FIG. 7 illustrates a comparison of different buffers C.

It must be clearly understood, however, that these Examples are given solely as an illustration of the subject of the invention, without in any way implying a limitation.

EXAMPLE 1

Treatment of a Sample of Bovine Brain for Assaying PrPres in the Field: Selection of the Appropriate Amount of Buffer B A 500 mg sample of bovine brain is ground and homogenized to a concentration of 25% (w/v) in 5% glucose solution.

To carry out the homogenization, the brain sample (500 mg) and 1 ml of glucose are introduced into tubes containing ceramic beads, with agitation. The supernatant (about 1.5 ml) is recovered; the beads are rinsed in suspension in 500 μl of glucose and agitated; the supernatant obtained is recovered and mixed with the previous supernatant (2 ml).

400 μl of homogenate as obtained above (equivalent to 100 mg of brain) are incubated with 400 μl of buffer A comprising a mixture of equal parts of 25% (w/v) SDS and 25% (v/v) Tween 80 in a ratio of 1/1 (v/v) and proteinase K (0.1 mg/ml buffer A, i.e. 0.4 mg/g tissue) for 10 minutes (2 times 5 min) at 37° C. (step (1)). As a variant, buffer A advantageously comprises 10% sarkosyl and 10% Triton X100; the latter buffer A, which does not comprise SDS, is more advantageous because it does not cause any perturbation in the detection of the PrPres by specific antibodies using a method of the ELISA type.

0 to 1000 μl of butanol (buffer B) are added (step (2)).

FIG. 1 shows the PrPres purification yield (%), quantified by western blotting, and the amount of residue (in mg) as a function of the amount of buffer B added.

This Figure shows that between 10 and 53% of butanol the PrPres is kept in suspension, and that between 30 and 50% a purification yield of the order of 100% and a residue of less than 10 mg are obtained.

After centrifugation at 3800 g (4000 rpm, JOUAN centrifuge) for 10 minutes (step (3)), the supernatant is discarded and the residue obtained, which contains the PrPres, is dissolved in 80–100 μl of a buffer C (step (4)) comprising:

either 0.5% SDS and 0.5 M urea, or Laemmli's buffer, or 0.5% sarkosyl and 6 M urea, for 5 minutes at 100° C.

The PrPres is dissolved by this treatment; the sample is ready for immediate use in an assay of the immunological type, such as ELISA or western blotting.

To perform an ELISA, the residue is preferably dissolved in a buffer C comprising sarkosyl (0.25–1%) and urea (0.25–8 M) or comprising SDS (0.25–1%) and urea (0.25–1 M); after heating, the sample obtained will preferably be diluted (to ¼ or ½) with a buffer containing albumin to give a final albumin concentration of between 2 and 10% (w/v), or with a buffer containing 1% deoxycholate.

As a variant, the diluted sample is heated at 100° C. for 5–10 minutes and then centrifuged for 2 to 10 minutes at a speed below 20,000 g, preferably at a speed of between 3500 g and 17,500 g; the supernatant is diluted to between ¼ and ½ with an ELISA buffer.

In the present case, the PrPres is quantified by western blotting, being mixed with an equal volume of Laemmli's buffer; the diluted sample is then deposited on gel for detection by western blotting; the amounts of PrPres detected are compared with a linear range of dilutions of PrPres purified under the same conditions as above from one and the same homogenate of bovine brain affected by BSE, at the terminal stage of the disease (positive control).

The samples treated by the method according to the invention are devoid of background and afford a reliable, specific and quantitative assay of the PrPres.

The method according to the invention allows a significant increase in the PrPres purification yield:

In fact, if only buffer A is added, the yield of PrPres is of the order of only 40%, so a loss of the order of 60% of the PrPres is observed, due especially to its partition between the solid phase and the liquid phase; moreover, there is a substantial amount of residue. This explains why the protocols described in the prior art use sarkosyl, which gives rise to smaller residues but necessitates cumbersome ultracentrifugations in order to obtain a sufficient yield.

Step (2) makes it possible to increase the yield of PrPres in the solid phase: a yield of the order of 80–100% is obtained in the solid phase of the, suspension S2 and the amount of residue is reduced at the same time, as explained above.

EXAMPLE 2

Treatment of a Sample of Bovine Brain for Assaying PrPres in the Field: Variant of Step (1) and Step (2)

The homogenization step is identical to that described in Example 1.

The 2 ml of homogenate obtained from the 500 mg of bovine brain are then incubated with 2 ml of buffer A under the same conditions as those described in Example 1 (step (1)).

3 ml of buffer B are added under the same conditions as those described in Example 1 (step (2)).

The remainder of the method is identical to that of Example 1.

EXAMPLE 3

Treatment of a Sample of Bovine Brain for Assaying PrPres in the Field: Variant of the Homogenization Step A 250 mg sample of bovine brain is ground and homogenized to a concentration of 25% (w/v) in 5% glucose solution.

To carry out the homogenization, the sample of brain (250 mg) and 750 µl of glucose are introduced into tubes containing ceramic beads, with agitation for 40 seconds (RIBOLYSER-HYBAID apparatus); 400 µl of supernatant arc withdrawn and the remainder of the procedure is as in Example 1.

EXAMPLE 4

Comparison of the Influence of Different Buffers B on the Ratio of the PrPres Purification Yield to the Amount of Residue The sample is treated under the same conditions as those described in Example 1 except that the amount of buffer B is 600 µl.

Figure 2:
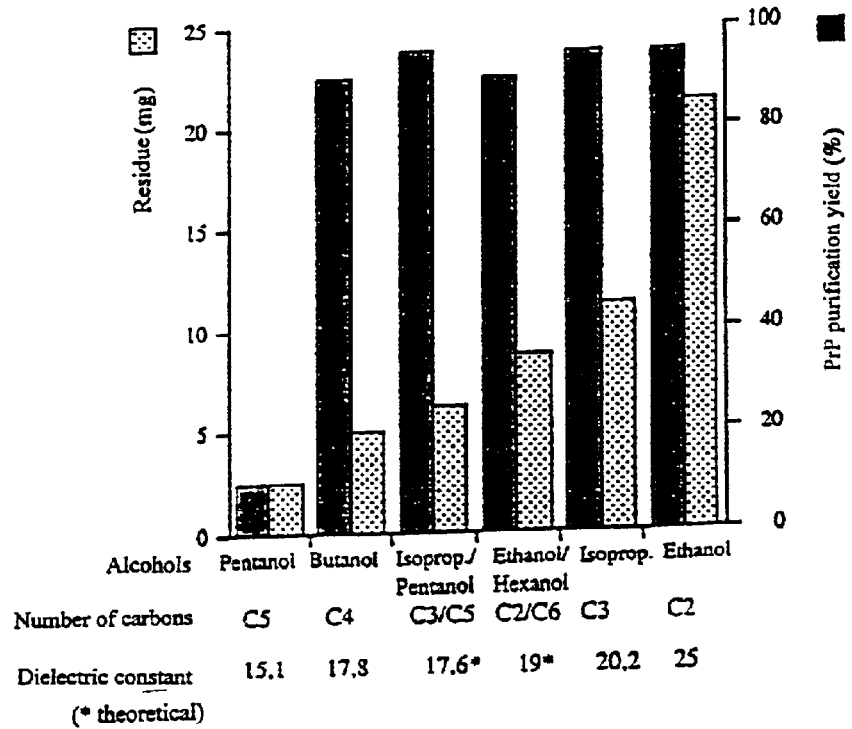

FIG. 2 illustrates the ratios obtained by western blotting with different buffers B: pentanol, butanol, isopropanol/pentanol mixture, ethanol/hexanol mixture, isopropanol and ethanol; the mixtures were made up by volume.

EXAMPLE 5

Comparison of the Dielectric Constants of Different Mixtures and Their Influence on the PrPres Purification Yield and the Amount of Residue The method is carried out under the conditions described in Example 4.

Figure 3A:
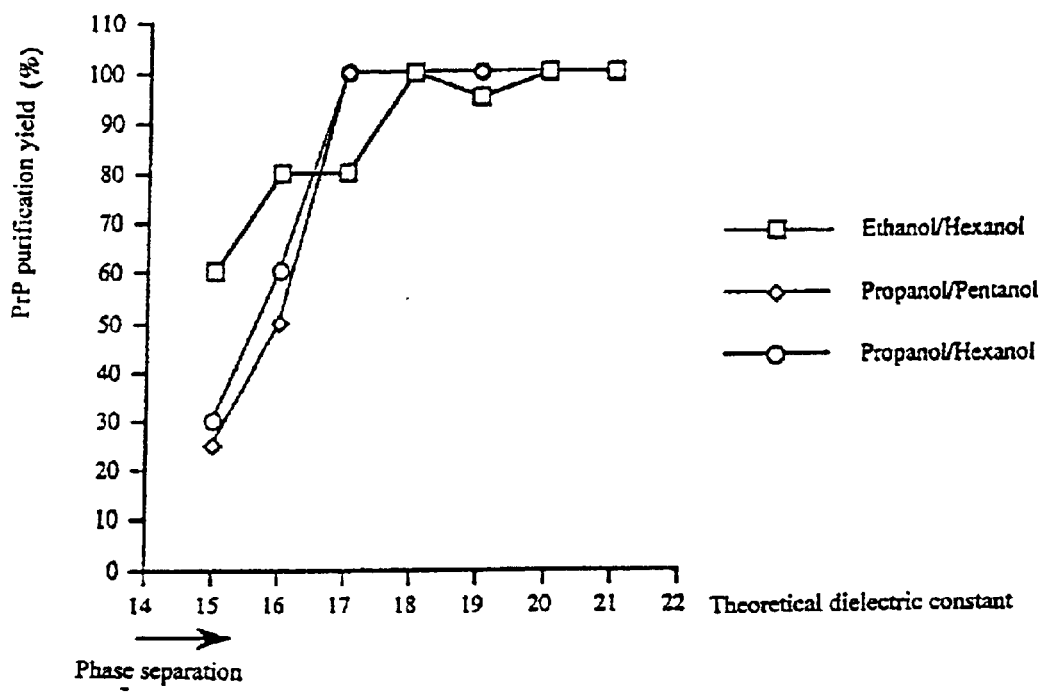
Figure 3B:
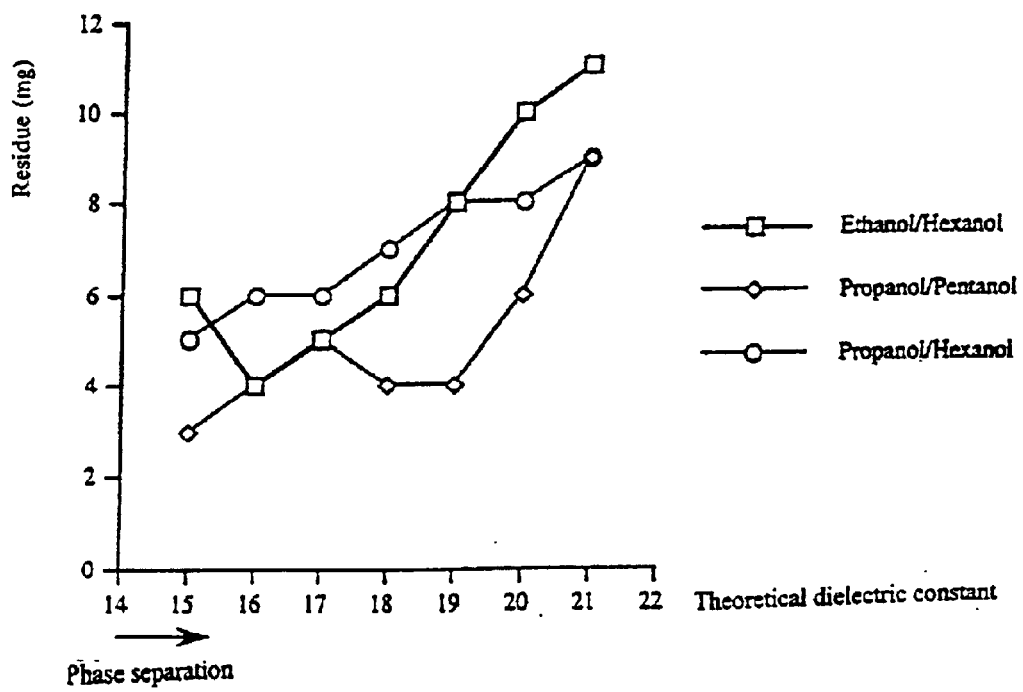

FIG. 3 illustrates the results obtained: in the case where buffer B is a mixture of alcohols, the volume of each alcohol is calculated as a function of its dielectric constant and the desired theoretical dielectric constant of the mixture (for example 17) and based on a total volume of alcohol of 600 µl. For example, the following formula is obtained for the hexanol/ethanol mixture:

$$13.y+25(1-y)=17$$

y being the percentage of hexanol, 13 being the dielectric constant of hexanol and 25 being the dielectric constant of ethanol.

For a mean theoretical dielectric constant of 15 or below, phase separation is observed.

EXAMPLE 6

Detection of PrPres by Western Blotting

*Protocol:

1) Incubation at 37° C., for 2 times 5 min. of 400 mg of 25% (weight/volume) bovine brain homogenate and 400 µl of buffer A comprising 400 µl of a mixture of equal parts (v/v) of 25% (w/v) SDS and 25% (v/v) Tween 80 (50/50) and proteinase K (PK) at a concentration of 0.1 mg/ml buffer A.

2) 600 µl of buffer B (or 1000 µl of buffer B for the samples of lanes 7 and 8), consisting of butan-1-ol, are added.

3) The mixture is centrifuged at 15,000 rpm for 5 min (about 17,000 g).

4) The centrifugation residue is taken up in 100 pi of Laemmli's buffer containing 4% SDS, and heated at 100° C. for 5 min.

*Western Blotting:

The samples obtained are used to perform SDS-PAGE and transferred to a nitrocellulose membrane under the conditions described by Towbin et al. (Proc. Natl. Acad. Sci. USA, 1979, 76, 4350–4354) or by C. I. Lasmézas et al. (J. Gen. Virol., 1996, op. cit.).

Before being deposited on the electrophoresis gel, the samples were diluted to 1/20 in a negative control produced under the same conditions as those described in Example 1 from a healthy bovine homogenate, because of the magnitude of the signals (12% polyacrylamide gel loaded with the equivalent of 10 mg (10 µl) of brain, corresponding to 9.5 mg of healthy bovine brain and 0.5 mg of infected bovine brain).

Immunodetection of the PrPres was effected with the antiserum JB007 (R. Demaimay et al., J. Virol., 1997, 71, 12, 9685–9689) (1/5000) and anti-rabbit goat Ig conjugated with peroxidase (1/2500). The immunoreactivity is revealed by chemiluminescence (ECL, Amersham), quantified and visualized on autoradio-graphic films, as illustrated in FIG. 4.

Figure 4:
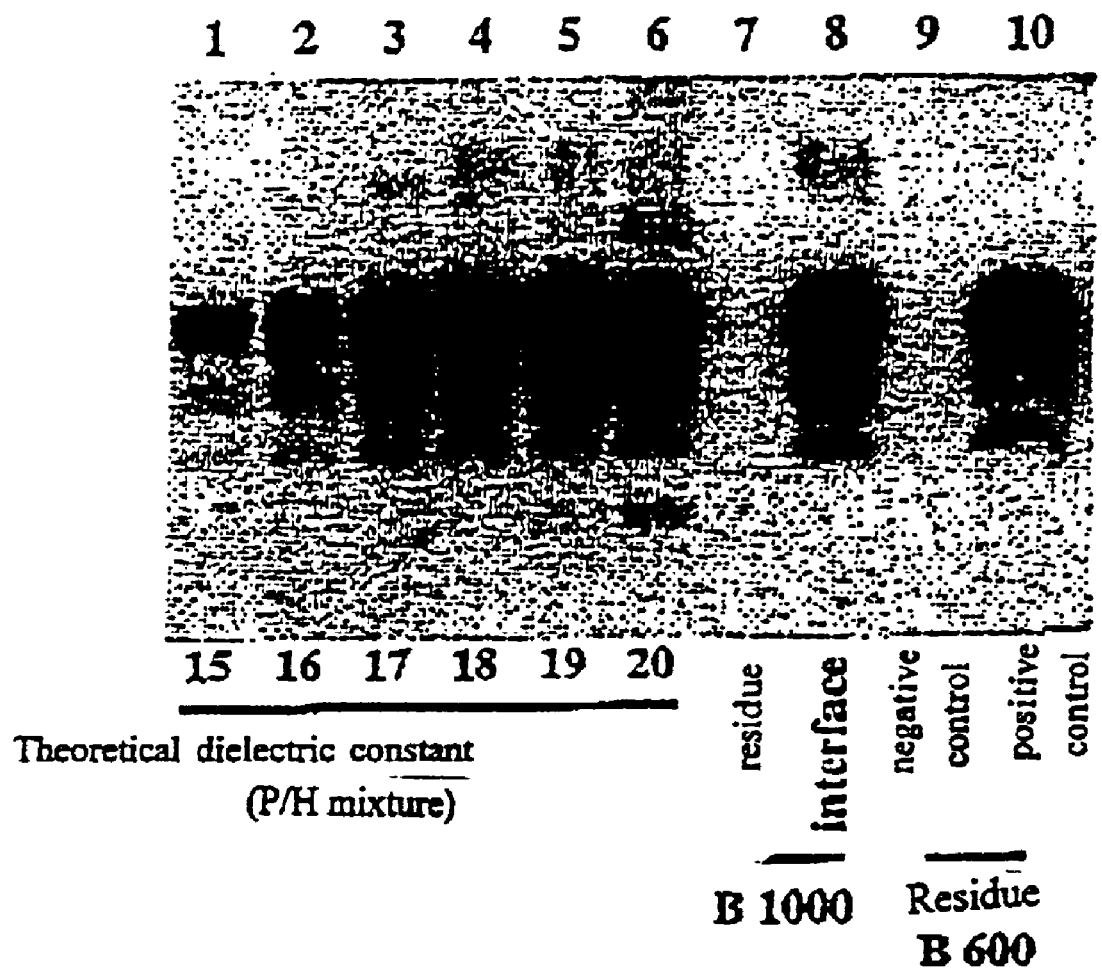
Figure 5:
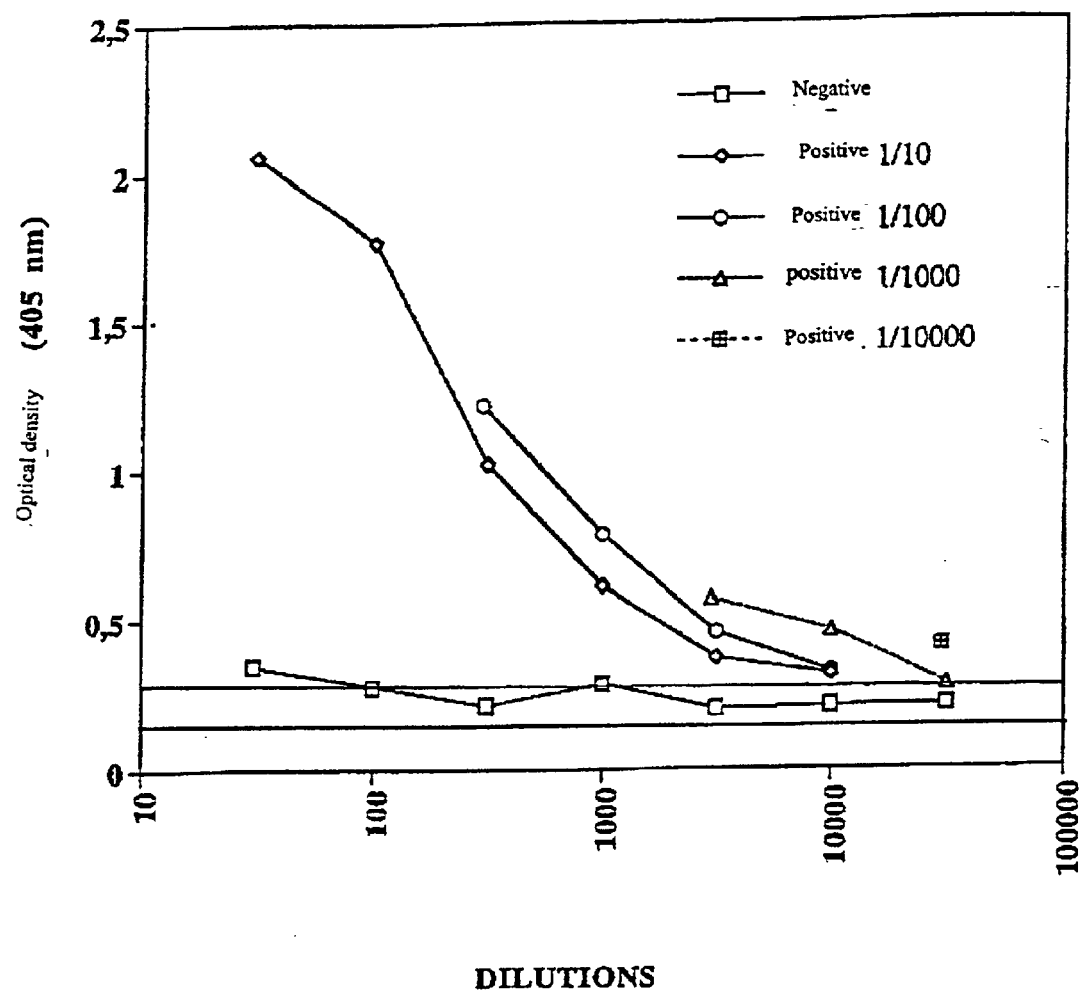
Figure 6:
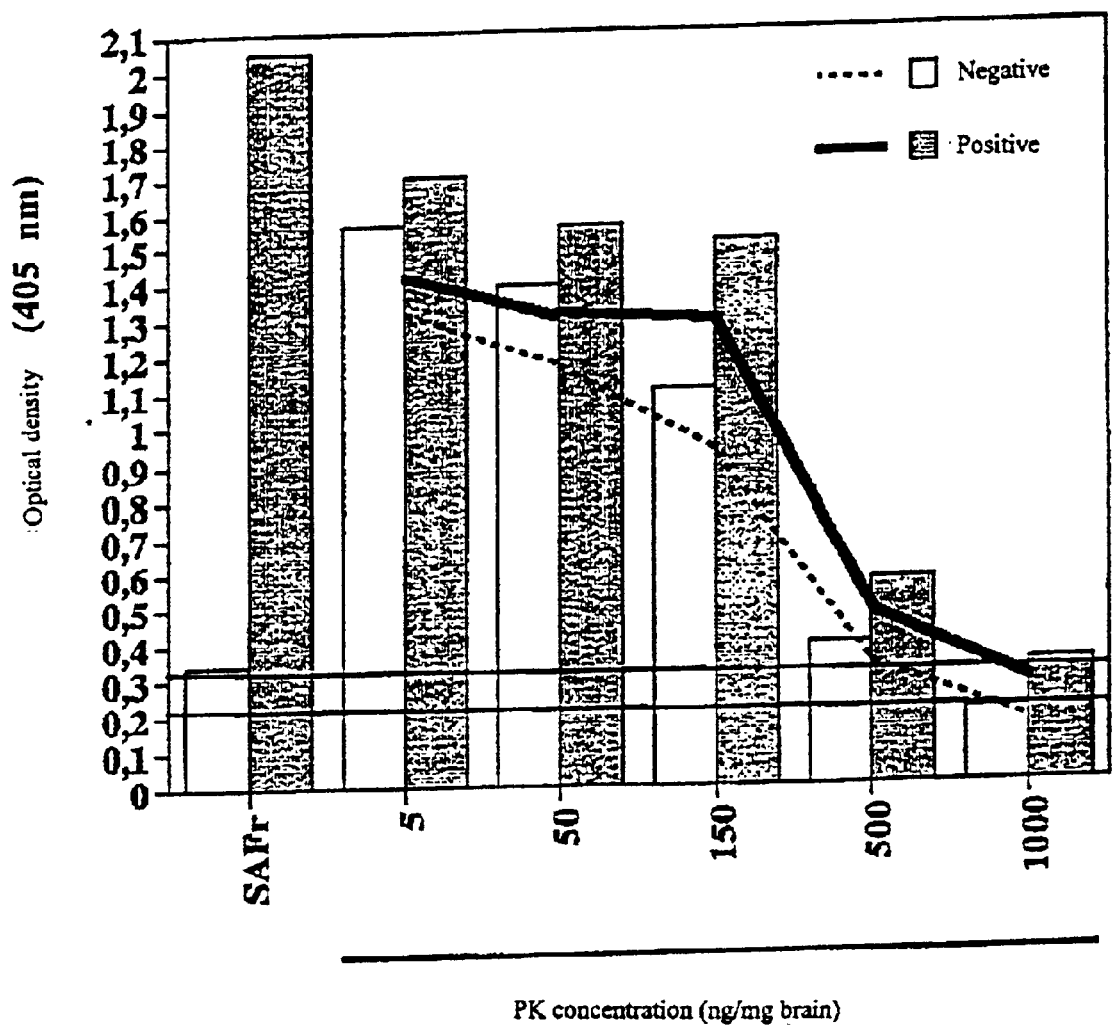
Figure 7:
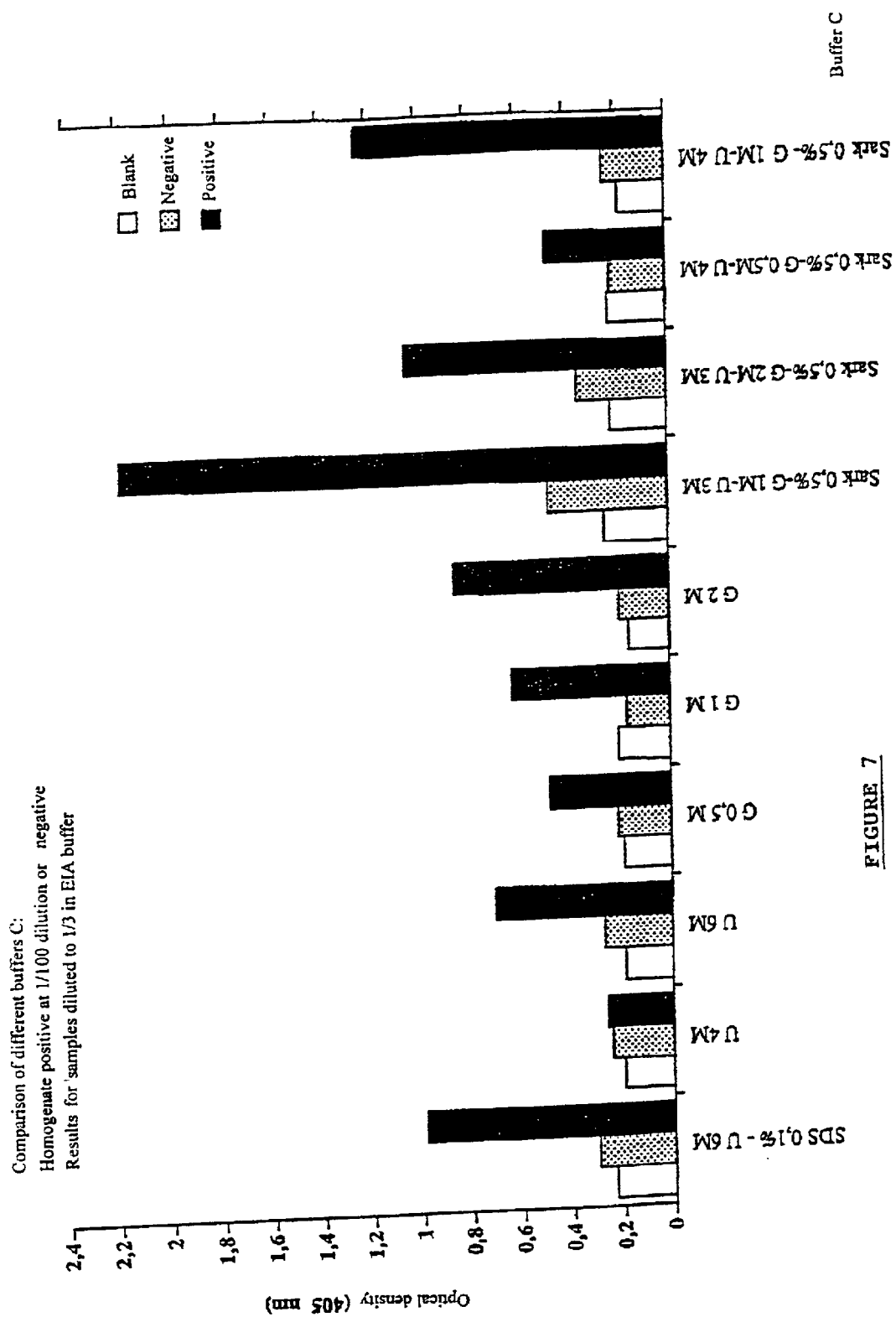

FIG. 4 illustrates the results obtained and corresponds to the propanol/hexanol curve of FIG. 3A.

In FIG. 4, lanes 1 to 6 correspond to samples treated using different propanol/hexanol mixtures as buffer B, leading to different mean theoretical dielectric constants; lanes 8 and 9 correspond to biological samples subjected to a procedure using 1000 μl of butanol as buffer B (53% on the abscissa of FIG. 1): it is observed in this case that all the PrPres ends up at the interface; lanes 9 and 10 correspond to biological samples subjected to a procedure using 600 μl of butanol as buffer B (43% on the abscissa of FIG. 1): it is observed in this case that all the PrPres ends up in the residue (lane 10), whereas no signal is observed in a negative control treated under the same conditions (lane 9).

EXAMPLE 7

ELISA of PrPres from a Sample Obtained According to the Invention

A sample is prepared under the following conditions:

A 400 mg sample of bovine brain is ground and homogenized to a concentration of 20% in 5% glucose solution (1.6 ml) under the same conditions as those described in Example 1.

500 μl of the homogenate obtained arc incubated at 37° C. for 10 min (2 times 5 min with intermediate agitation) with 500 μl of buffer A comprising 10% sarkosyl and 10% Triton X100, together with proteinase K (80 μg/ml).

500 μl of buffer B (butanol) are added.

The mixture is centrifuged for 5 min at 15,000 rpm with a rotor capable of producing 17,608 g; the same results are obtained with a centrifugation time of 4 min at 20,627 g.

The supernatant is discarded and the residue obtained, which contains PrPres, is dissolved for 5 min at 10° C. in 100 μl of buffer C comprising 6 M urea and 0.5% sarkosyl.

The mixture is centrifuged for 5 min at 15,000 rpm with a rotor capable of producing 17,608 g; the same results are obtained with a centrifugation time of 4 min at 20,627 g. The supernatant is diluted to 1/3 in EIA buffer (phosphate buffer with 0.5% deoxycholate).

To perform the ELISA, the sample obtained is deposited at a rate of 100 μl per well, in duplicate, on a plate covered with a first anti-PrP antibody (8G8, ref. Kraseman et al., Molecular Medicine, 1996); this is followed by incubation, washing and developing with a second anti-PrP antibody (12F10, ref. Kraseman et al., 1996) coupled with acetylcholinesterase (ref. Grassi et al., J. Immunol. Methods, 1989). After incubation with the substrate for acetylcholinesterase, the results are read at 415 nm 15 min or 30 min after addition of the substrate (Ellmann's reagent).

The results shown in FIG. 5 relate to a 20% (weight/volume) homogenate of bovine brain clinically affected by BSE, diluted to 1/10, 1/100, 1/1000 or 1/10,000 in a 20% (weight/volume) homogenate of healthy bovine brain.

The samples are then treated under the conditions described above and tested by EIA with 8G8 as the capturing antibody and 12F10 as the detecting antibody.

The samples are tested diluted in the EIA depot buffer (dilutions to 1/3, then by factors of 3).

FIG. 5 illustrates the results obtained (optical density of the signal as a function of the final dilution of the homogenate, i.e. dilution in the negative homogenate× dilution in the EIA buffer): the semilogarithmic curve has the sigmoid shape conventionally observed in all assays of the EIA type. Furthermore, it is pointed out that there is a good superposition of the curves obtained from the homogenates diluted to 1/10, 1/100 and 1/1000. Finally, the sensitivity level of the test makes it possible to detect this positive brain diluted to 1/10,000.

In FIG. 6, another homogenate diluted to 1/100 was tested by the EIA technique, either after treatment as described above with a PK concentration of 400 ng/mg, or after direct treatment of the homogenates with different PK concentrations. It is found that direct treatment of the homogenates with PK, without purification, gives either high signals of the negative controls for low PK concentrations (incomplete destruction of PrPc), or low signals for the positive cows with high PK concentrations. This Example therefore emphasizes that it is essential to treat the homogenates in the manner described above if the PrPres is to detected correctly.

EXAMPLE 8

Comparison of Different Buffers C

The sample treatment protocol used is that of Example 7. FIG. 7 illustrates the results obtained.

Guanidine seems to be advantageous and the urealguanidine combination appears to be the most valuable (in the knowledge that urea is better tolerated by ELISA).

As is apparent from the foregoing description, the invention is in no way limited to those modes of execution, embodiments and modes of application which have now been described more explicitly, on the contrary, it encompasses all the variants thereof which may occur to those skilled in the art, without deviating from the framework or the scope of the present invention.

What is claimed is:

1. A method of purifying abnormal form of prion protein (PrPres) from a biological sample, comprising therefor:

(1) the incubation, for 30 seconds to 2 hours, at a temperature below 80° C., of said biological sample with a buffer A comprising at least one surfactant in an amount of between a quarter and four times the weight of the biological sample, and optionally prior, subsequent or simultaneous incubation with a protease, to form a suspension S1;

(2) the addition, to said suspension S1 obtained in (1), of a buffer B in an amount suitable for clarifying said suspension by forming a microemulsion or a microsuspension, said buffer B consisting of a solvent or solvent mixture which does not solubilize the PrPres and has a dielectric constant of between 10 and 25, to form a suspension S2;

(3) the centrifugation of the suspension S2 to form a residue; and (4) the solubilization of said residue in a buffer C comprising at least one compound selected from the group consisting of: (i) one surfactant, as defined in step (1), at a concentration of between 0.1% and 5%, based on the volume of buffer C (w/v), (ii) one chaotropic agent at a concentration of between 0.1 M and 8 M, and (iii) a mixture of compound (i) and compound (ii), at a temperature between room temperature and 100° C., to form a solution.

2. The method according to claim 1, wherein in step 1 the incubation time is between 30 seconds and 10 minutes.

3. The method according to claim 1, wherein buffer A comprises a surfactant selected from the group consisting of:

anionic surfactants such as SDS (sodium dodecylsulfate), sarkosyl (lauroylsarcosine), sodium cholate, sodium deoxycholate or sodium taurocholate;

zwitterionic surfactants such as SB 3-10 (decyl sulfobetaine), SB 3-12 (dodecyl sulfobetaine), SB 3-14, SB 3-16 (hexadecyl sulfobetaine), CHAPS or deoxy-CHAPS;

non-ionic surfactants such as C12E8 (dodecyl octaethylene glycol), Triton X100, Triton X114, Tween 20, Tween 80, MEGA 9 (nonanoylmethylglucamine), octylglucoside, LDAO (dodecyldimethylamine oxide) or NP40; and surfactant mixtures such as a mixture of an ionic surfactant and a non-ionic surfactant, a mixture of two ionic surfactants or a mixture of an ionic surfactant and a zwitterionic surfactant.

4. The method according to claim 1, wherein in step (1), the amount of surfactant present in buffer A is between a quarter and one and a half times the weight of the biological sample.

5. The method according to claim 1, wherein buffer B is selected from the group consisting of $C_3$–$C_6$ alcohols and alcohol mixtures with a mean theoretical dielectric constant of between 10 and 25.

6. The method according to claim 1, wherein the following alcohols or alcohol mixtures are selected from the group consisting of butan-1-ol, butan-2-ol, 2-methylpropan-1-ol, isopropanol, isopropanol+pentanol, ethanol+hexanol and butanol+pentanol.

7. The method according to claim 1, wherein buffer C comprises a chaotropic agent which is selected from the group consisting of urea, guanidine, and mixtures of urea and guanidine.

8. The method according to claim 1, wherein the solubilization step comprises heating at a temperature equal to or greater than 80° C. for 5 to 10 minutes, followed by centrifugation.

9. The method of claim 1, wherein the concentration of the surfactant in buffer C is between 0.25% and 1% and the temperature of the solubilization step is between 80° C. and 100° C.

10. A method of claim 1, further comprising the step of homogenizing the biological sample before it is suspended in Buffer A.

11. The method according to claim 1, wherein buffer C comprises a surfactant selected from the group consisting of:

anionic surfactants selected from the group consisting of SDS (sodium dodecylsulfate), sarkosyl (lauroylsarcosine), sodium cholate, sodium deoxycholate or sodium taurocholate;

zwitterionic surfactants selected from the group consisting of SB 3-10 (decyl sulfobetaine), SB 3-12 (dodecyl sulfobetaine), SB 3-14, SB 3-16 (hexadecyl sulfobetaine), CHAPS or deoxyCHAPS;

non-ionic surfactants selected from the group consisting of C12E8 (dodecyl octaethylene glycol), Triton X100, Triton X114, Tween 20, Tween 80, MEGA 9 (nonanoylmethylglucamine), octylglucoside, LDAO (dodecyldimethylamine oxide) or NP40; and surfactant mixtures selected from the group consisting of a mixture of an ionic surfactant and a non-ionic surfactant, a mixture of two ionic surfactants or a mixture of an ionic surfactant and a zwitterionic surfactant.

12. A method of claim 1, further comprising:
(1) the addition at step 2, to said suspension S1, of buffer B in an amount suitable for creating a phase separation;
(2) following centrifugation of suspension S2, recovery of a film present at the interface;
(3) resolubilization of the film with buffer A without the addition of protease;
(4) centrifugation of a suspension obtained in step (3) to produce a residue soluble in buffer C.

13. The method of claim 12, wherein the concentration of the surfactant in buffer C is between 0.25% and 1% and the temperature of the solubilization step is between 80° C. and 100° C.

14. The method according to claim 1, wherein the temperature used in step (1) is between room temperature and 50° C.

15. The method of claim 14, wherein the temperature used in step 1 is about 37° C.

16. The method according to claim 1, wherein the centrifugation of step (3) is carried out for 2 to 10 minutes at a speed below 20,000 g.

17. The method of claim 16, wherein the centrifugation speed is between 3500 g and 17,500 g.

18. A method of claim 1, further comprising the step of detecting the PrPres contained in the solution obtained at the end of step 4 by reacting it with a labeled anti-PrPres antibody.

19. A method of claim 18, wherein the solution containing the PrPres is diluted prior to the detection step.

20. A kit for treating a biological sample for the purpose of purifying PrPres from said biological sample, comprising, in addition to a buffer for homogenizing said biological sample, appropriate amounts of (i) a buffer A, selected from the group consisting of
anionic surfactants selected from the group consisting of SDS (sodium dodecylsulfate), sarkosyl (lauroylsarcosine), sodium cholate, sodium deoxycholate and sodium taurocholate;
zwitterionic surfactants selected from the group consisting of SB 3-10 (decyl sulfobetaine), SB 3-12 (dodecyl sulfobetaine), SB 3-14, SB 3-16 (hexadecyl sulfobetaine), CHAPS and deoxyCHAPS;
non-ionic surfactants selected from the group consisting of C12E8 (dodecyl octaethylene glycol), Triton X100, Triton X114, Tween 20, Tween 80, MEGA 9 (nonanoylmethylglucamine), octylglucoside, LDAO (dodecyldimethylamine oxide) and NP40; and
surfactant mixtures selected from the group consisting of a mixture of an ionic surfactant and a non-ionic surfactant, a mixture of two ionic surfactants and a mixture of an ionic surfactant and a zwitterionic surfactant;

(ii) a buffer B selected from the group consisting of C3–C6 alcohols and alcohol mixtures with a mean theoretical dielectric constant of between 10 and 25;

(iii) a buffer C which comprises a chaotropic agent which is selected from the group consisting of urea, guanidine, and mixtures of urea and guanidine; and (iv) an anti-PrPres antibody.

* * * * *